(12) United States Patent
Holthe

(10) Patent No.: US 7,559,690 B2
(45) Date of Patent: Jul. 14, 2009

(54) X-RAY POSITIONING DEVICE

(76) Inventor: Jared Holthe, 6386 Pheasant La., Verona, WI (US) 53593

( * ) Notice: Subject to any disclaimer, the term of this patent is extended or adjusted under 35 U.S.C. 154(b) by 0 days.

(21) Appl. No.: 11/956,044

(22) Filed: Dec. 13, 2007

(65) Prior Publication Data

US 2009/0154654 A1 Jun. 18, 2009

(51) Int. Cl.
G21K 4/00 (2006.01)
H05G 1/00 (2006.01)

(52) U.S. Cl. .......................... 378/192; 378/208

(58) Field of Classification Search .............. 378/20, 378/51, 62, 79, 192, 208, 209; 5/600, 601, 5/608
See application file for complete search history.

(56) References Cited

U.S. PATENT DOCUMENTS

| | | | |
|---|---|---|---|
| 2,552,592 A | 5/1951 | Rush | |
| 3,256,611 A | 6/1966 | Deming | |
| 3,328,582 A | 6/1967 | Morel | |
| 3,700,894 A | 10/1972 | Counsell | |
| 5,917,884 A | 6/1999 | Lee | |
| 6,217,214 B1 * | 4/2001 | Cabral et al. | 378/196 |
| 6,968,033 B2 * | 11/2005 | Lebovic et al. | 378/37 |
| 2008/0137813 A1 * | 6/2008 | Umeda | 378/208 |

* cited by examiner

Primary Examiner—Irakli Kiknadze
(74) Attorney, Agent, or Firm—Foley & Lardner LLP

(57) ABSTRACT

An apparatus for positioning a patient during an X-ray comprising a base, a turntable, wherein the turntable is rotatably attached to the base, with a foot guide and level. The side foot guide is attached to the turntable, while the foot plate is adjustable. A patient places his or her feet against the side foot guide with the heel against the foot plate during the exposure of the X-ray. The X-ray is taken with a level reference strip apparatus that allows the X-rays to be evaluated precisely and correctly.

19 Claims, 5 Drawing Sheets

X-RAY POSITIONING DEVICE

FIELD

The present invention relates generally to the field of radiology, and more specifically to X-ray system alignment with respect to patients and apparatuses.

BACKGROUND

The use of X-ray to diagnose medical conditions is ubiquitous throughout the medical and chiropractic professions. Diagnosis of osteopathic conditions, cancers, spinal misalignments, and a myriad of other conditions via X-rays are made on a daily basis. Sometimes, the X-rays are a one-time picture of the condition, and repeated X-rays are not necessary. Other times, repeated X-ray diagnosis and analysis over a period of time is necessary for comparative purposes. In such cases, the exact positioning of the patient for successive X-ray analysis is needed in order to accurately gauge the progression or healing of a given condition. For example, chiropractors routinely require specific positioning of a patient from one X-ray to the next to follow disease or healing progression over time.

In the chiropractic field for example, a chiropractor may use X-rays of the spine to diagnose a leg length difference, causing back pain. Over time, the chiropractor takes a number of X-ray images of the spine as the patient is adapting to a corrective lift in the shoe. This type of work needs to be done with precision, and it is important that the patient is positioned correctly for each film in the series. It is also important to know that the foundation the patient is standing on and the x-ray machine itself are level. Without positioning the patient in the same position for the X-ray every time, comparing a time-series of X-ray images can be a difficult, and error-filled process. There are many uncontrolled variables in patient positioning, including, but not limited to how the patient is standing or who is taking the films. Current X-ray images do not capture information on patient positioning.

A typical chiropractic X-ray system for imaging consists of a mounted cassette holder and an X-ray source. The cassette holder holds a film cassette or cartridge which in turn holds the X-ray film. The cassette holder is usually mounted on the wall, or to a post or tube that allows an X-ray technician, or other medical professional, to move the cassette holder up or down. The X-ray source, which can also be moved, is typically positioned some distance away (e.g. 40 to 72 inches) from the cassette holder. During X-ray exposure, a patient stands in front of the cassette holder so that he/she is positioned between the cassette holder and the X-ray source. The cassette holder and X-ray source are adjusted so that the exposure will image the correct part of the body.

Frequently, the patient simply stands in front of the cassette holder. However, patients may stand in a slightly different position from one X-ray to the next, causing mal-positioning and errors. The problem of mal-positioning is most significant when performing a comparison of a time-series of images. Without a way of accurately positioning the patent every time, it is unlikely that a patient will assume the same standing position, in the same location for each exposure of a time-series of X-rays that may take many months to accumulate.

A variety of different restraining devices are available to promote positioning consistency in images. The devices include head braces, exposure chairs, and straps. However, these devices are cumbersome and can be uncomfortable for the patient. Some restraining devices can only adapt to a small range of patient sizes. The technician spends a large amount of time helping the patient into the restraining device. Additionally, elaborate restraining devices are very expensive to purchase and maintain.

Therefore, a need exists for a patient positioning apparatus and method that allows a radiologist, chiropractor, or other medical professional to accurately acquire, and easily compare time-series exposures. There is also a need for a patient positioning apparatus and method that is inexpensive, quick to setup, and easy to use.

SUMMARY

In one aspect, an apparatus is provided comprising: a base; a turntable, wherein the turntable is rotatably attached to the base; and a foot guide; wherein, the apparatus is capable of positioning a patient for X-ray exposure. In some embodiments, the foot guide comprises two side plates and a heel stop. In other embodiments, the apparatus further comprises a level.

In some embodiments, the apparatus further comprises a locking knob, wherein the locking knob is capable of preventing the turntable from rotating. Hence, when the locking knob is loosened the turntable may rotate, but when the locking knob is tightened the turntable is prevented from rotating.

In other embodiments, the apparatus further comprises adjustable feet. The adjustable feet are thus capable of leveling the base.

In yet other embodiments, the base has graduation marks and the turntable has a reference mark; such that the graduation marks and the reference mark indicate the angle of the turntable relative to the base.

In another aspect, an apparatus is provided comprising a main body, a first mounting pad, a second mounting pad, and a reference strip, wherein the apparatus is an X-ray image leveling apparatus and an image of the reference strip appears on an X-ray image. In some embodiments, the apparatus comprises a level. In other embodiments, the main body, the first mounting pad, and the second mounting pad are made of X-ray transparent materials. In some embodiments, the body is attached to the first mounting pad via a first locking knob. In other embodiments, the body is attached to the second mounting pad via a second locking knob. In yet other embodiments, the body is attached to the first mounting pad via a first locking knob, and the body is rotatably connected to the second mounting pad.

In another aspect, a method for taking X-rays is provided comprising: positioning a patient using a patient positioning apparatus to position a patient at a specific angle; exposing the patient to an X-ray source; and acquiring an X-ray image; wherein the patient positioning apparatus comprises a base; a turntable, and a foot guide; the turntable is rotatably attached to the base; and a patient's feet contact the foot guide during the exposure to the X-ray source. In some embodiments, the methods further comprise analyzing the X-ray using knowledge of the specific angle. In yet other embodiments, the method further comprises analyzing a series of X-rays using knowledge of the specific angle for each X-ray in the series.

In a further aspect, a method of referencing a level in an X-ray image is provided comprising leveling an X-ray reference and taking an X-ray, wherein the X-ray reference comprises a main body; a first mounting pad; a second mounting pad; a level and, a reference strip, and wherein an image of the reference strip appears on an X-ray image. In some embodiments, the method further comprises analyzing the X-ray using the image of the reference strip.

In yet another aspect, a method is provided comprising using an X-ray reference to aid in leveling a cassette holder associated with an X-ray machine after installation of the X-ray machine, wherein the X-ray reference comprises a main body; a first mounting pad; a second mounting pad; a level; and a reference strip, wherein an image of the reference strip appears on an X-ray image. In some embodiments, the method further comprises comparing the image of the reference strip on an X-ray film with an edge of the X-ray film; determining if the cassette holder is level; and making any needed leveling adjustments to the cassette holder.

DETAILED DESCRIPTION

Figure 1:
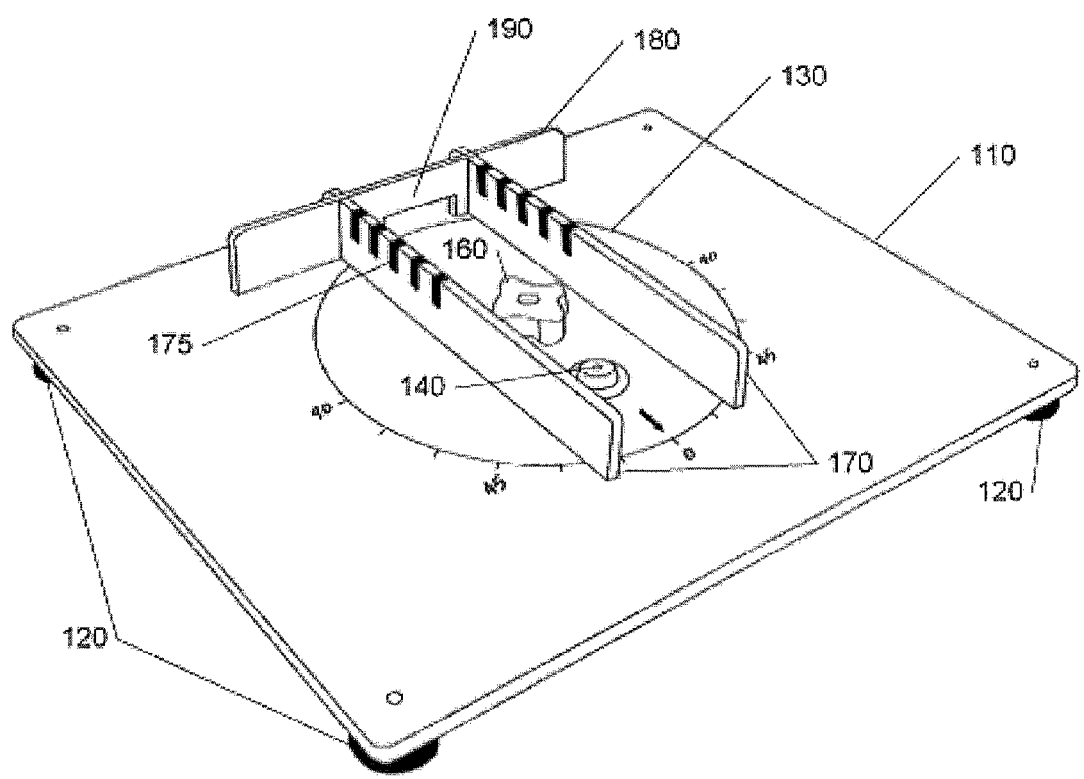
FIG. 1 is an isometric view of a patient positioning apparatus.
Figure 2:
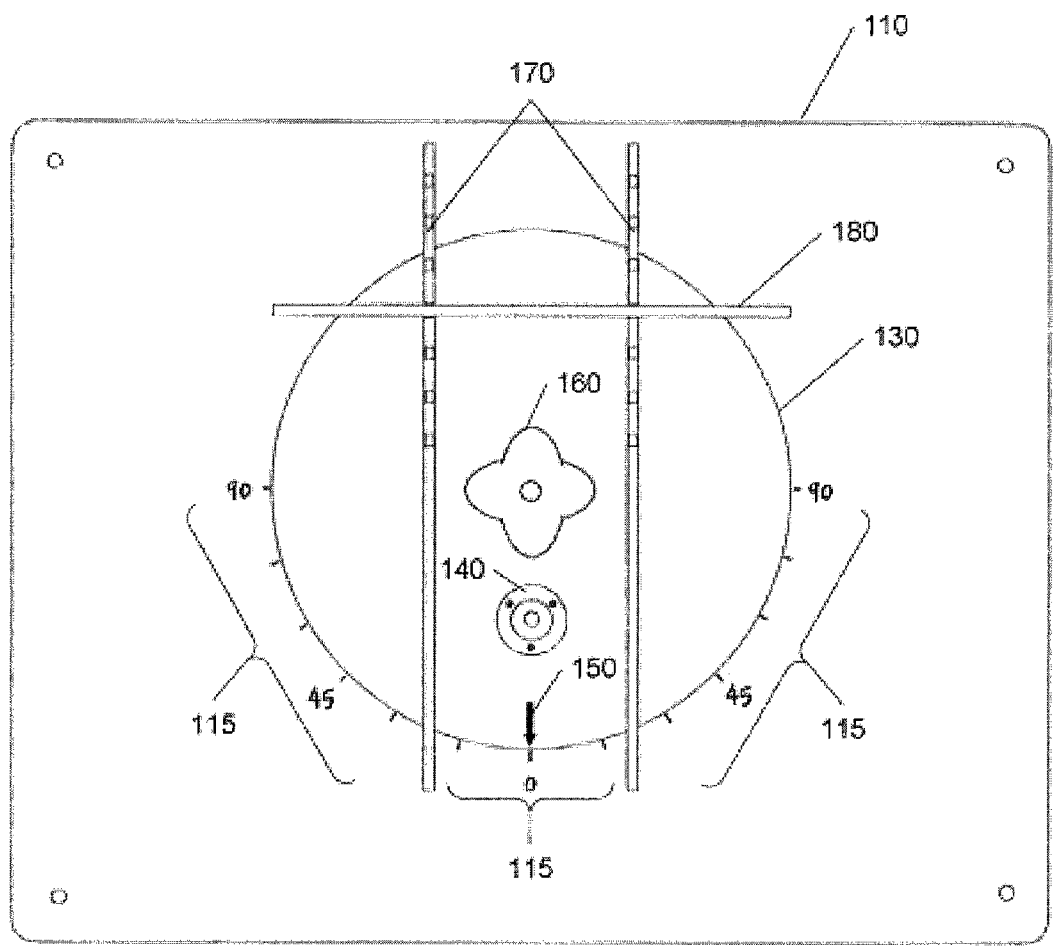
FIG. 2 is a top view of the patient positioning apparatus of FIG. 1.
Figure 3:
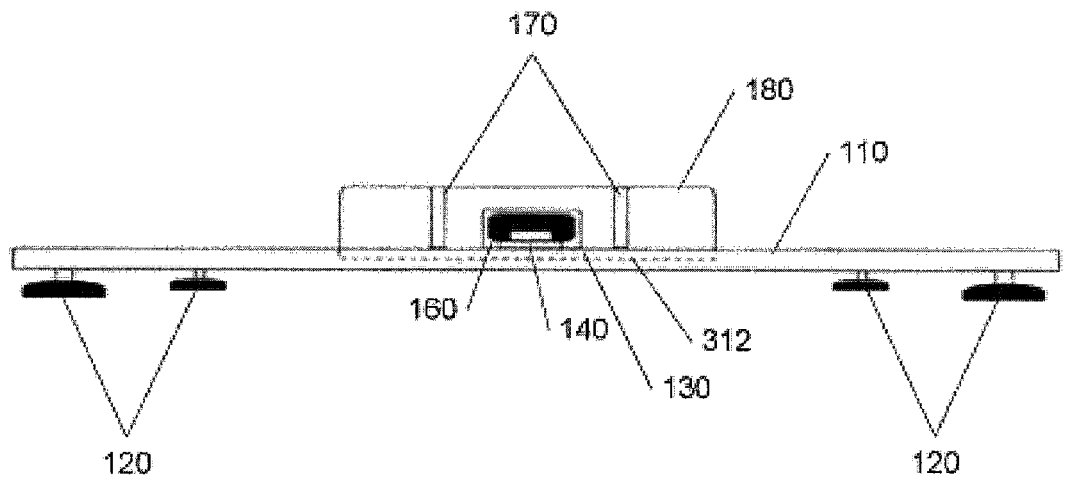
FIG. 3 is a front view of the patient positioning apparatus of FIG. 1.

Referring to FIGS. 1-3, a patient positioning apparatus 100 is described. In FIG. 1, an isometric view of a patient positioning apparatus 100 is shown. The patient positioning apparatus 100 includes a base 110 and a turntable 130. The base 110 can be made from any of a number of structurally sound materials such as metals, plastics, ceramics, and other such materials known to those of skill in the art. For example, while any of a number of metals may be used, stainless steel and aluminum are but two. The base 110 can be made using different techniques such as casting or machining. The base 110 should be of sufficient size so that a patient may comfortably stand on a top surface.

The base 110 is supported by four or more feet 120. The feet 120 can be made of any of a variety of materials, including but not limited to plastics, metals, ceramics, wood, glass, rubber, or other materials known to those of skill in the art. In some embodiments, the feet 120 are coated with a non-slip material, and in other embodiments, the feet 120 are constructed of rubber. In still other embodiments the feet can be directly fastened or bolted to the floor to ensure its proper position. The feet 120 can be individually adjusted to change the height and skewness of the base 110. The base 110 may also include a handle (not shown) so that the patient positioning apparatus 100 can be easily moved.

To the top of the base 110 is attached a turntable 130. In some embodiments, the turntable 130 is engaged in a recessed area, or cutout, in the base 110, with the top of the base 110 and the top of the turntable 130 being flush, or at least nearly flush. The turntable 130 is pivotally connected to the base 110. Such a connection may be via a bolt, a rod, a rivet, or via a locking knob 160 as described below. Hence, the turntable 130 can spin freely within the base 110. Alternatively, a turntable is positioned above a base, with the center of the turntable being pivotally connected to the base. The interface between the base 110 and the turntable 130 can also include a bearing race, or other friction reducing method as is well known in the art.

In some embodiments, the base 110 and the turntable 130 can be connected by a locking knob 160, such that while the turntable 130 is pivotally connected to the base 110, movement may be arrested by the locking knob 160. The locking knob 160 has a threaded end that is inserted through a hole in the center of the turntable 130 and threaded into a threaded hole in the center of the cutout of the base 110. A user tightens the locking knob 160 to lock the base 110 and the turntable 130 together. Alternatively, a threaded post may be pressed into the base 110 or a standard bolt may be used for the locking knob 160. Additionally, the recessed area, or cutout in the base 110, and also the turntable 130 may include teeth that engage when the plates contact one another. As is well known in the art, various methods are known for securing a turntable.

In some embodiments, the turntable 130 also includes a level 140. The level 140 may be a bubble-type dome level, or the level may be two orthogonally situated levels that are both used to level the base 110 or the turntable 130. Such levels may be used to level a plane, as opposed to only one axis. Alternatively, a level that is not connected to the turntable may be placed on the base 110, while the feet 120 are adjusted to a level position.

In some embodiments, a foot guide is attached to the turntable 130 so that the foot guide and the turntable 130 move together. The foot guide can be attached to the turntable 130 by welding, rivets, screws, or any other method of fastening. The foot guide consists of two side plates 170 that will accommodate a variety of foot sizes. The two side plates 170 of the foot guide are parallel in some embodiments; however, they can also be set off at an angle, in other embodiments. The side plates 170 of the foot guide can also be contoured to the shape of a foot. The side plates 170 of the foot guide are centered about the center of the turntable 130 along one axis, and off-center with regard to the orthogonal axis in the same plane. Such centering and off-centering are readily illustrated in FIG. 2, where it is shown that the side plates 170 are centered with respect to a vertical axis along the center of the turntable 130, but are off-center with respect to the horizontal axis along the center of the turntable 130. As described, the vertical and horizontal axes are within the plane of the surface of the apparatus 100.

A heel stop 180, may also be included in the foot guide. The heel stop 180 straddles the two plates 170 of the foot guide. The user can move the heel stop 180 from one set of notches to another by using a heel stop handle 190. Each of the two plates 170 of the foot guide include a series of notches 175 to allow for various foot and body sizes. Movement of the heel stop 180 from one set of notches to another allows patients of varying sizes to use the patient positioning apparatus 100. The heel stop handle 190 allows the user to easily grip the heel stop 180 so it can be adjusted. A patient may place the inside of his or her feet tight against each of the side plates 170 of the foot guide, and the heel of each foot against the heel stop 180. Hence, the patient's feet are now in a "fixed" position relative to the base.

Referring now to FIG. 2, a top view of the patient positioning apparatus of FIG. 1 is shown. The base 110 has graduation marks 115 etched into it around the edge of the cutout for the turntable 130. The graduation marks 115 denote reference angles relative to the circumference of the turntable cutout. The graduation marks 115 can also be decals, silk-screened onto the base 110, or molded, stamped, or cast into the base 110 as is well known in the art.

Likewise, the turntable 130 can have a reference mark 150. The reference mark 150 represents the center line between the two side plates 170 of the foot guide. Hence, when the turntable 130 is moved, the user can determine the angle the turntable 130 has been moved relative to the base 110. Consequently, the user can determine the angle of the patient's feet relative to the base 110. Alternatively, the patient positioning apparatus can include a electronic position sensor and numerical read-out such as the type used on a machining mill. In addition, the turntable may also have spring-loaded lock bearings or a spring-loaded catch to aid in locking the turntable at predetermined, specific, graduated intervals.

Referring to FIG. 3, a frontal view of a turntable cutout 312 is visible. The turntable cutout 312 is cylindrical and approximately 0.25" in depth. The turntable 130 sits in the turntable cutout 312. When the user tightens the locking knob 160, the bottom of the turntable 130 presses against the bottom of the turntable cutout 312, locking the turntable 130 and the base 110 together.

Advantageously, the patient positioning apparatus allows a technician to easily determine the angle of the patient's feet relative to the base, and the leveling capabilities ensure that the patient is standing on a level platform in the same position for X-rays taken over time. Additionally, the patient positioning apparatus can be easily adjusted to compensate for different feet lengths and body sizes. Moreover, the patient positioning apparatus encourages the patient to stand at a specific angle relative to the base and in a specific manner.

Figure 4:
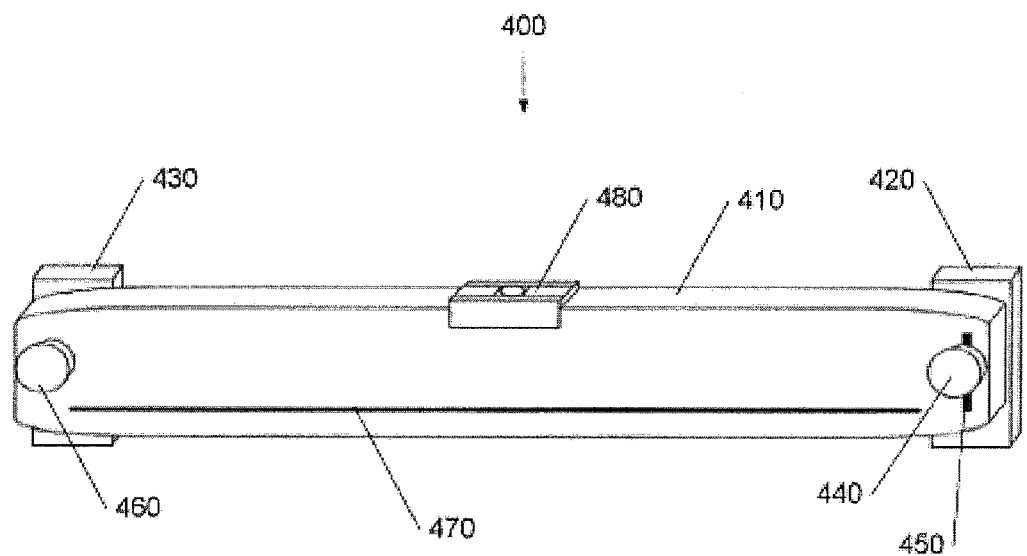
FIG. 4 is a perspective view of a X-ray reference apparatus.

Referring now to FIG. 4, perspective view of an X-ray reference apparatus 400 is shown. The X-ray reference apparatus 400 includes a main body 410, a first mounting pad 420, a second mounting pad 430, a leveling device 480, and a reference strip 470. The main body 410 may be adjustably mounted to the mounting pads 420, 430 such that one end of the body is capable of fine adjustment to perfectly level.

As shown in FIG. 4, the ends of the main body 410 have locking knobs 440, 460 that allow for leveling adjustment of the main body 410. The first mounting pad 420 is attached to one end of the main body 410 through an elongated hole 450, using first locking knob 440. The second mounting pad 430 pivots on one end of main body 410, with a second locking knob 460 being used to lock the main body 410 against the second mounting pad 430. In some embodiments, a second mounting pad is attached to a main body using a pivoting rivet or like device to allow for vertical adjustment, rather than the locking knob 460.

The first mounting pad 420 and the second mounting pad 430 can include foam adhesive pads such as the type where the user peels off a protective membrane and then affixes the first mounting pad 420 and the second mounting pad 430 to a surface, for instance, a cassette holder. The first mounting pad 420 and the second mounting pad 430 may also be attached to a surface with a hook-and-loop fastener, glue, suction cups, standard fasteners like screws or rivets, or any other means known to those of skill in the art.

The main body 410 of the X-ray reference apparatus 400 has a level 480. The level 480 is a bubble-type level. After the first mounting pad 420 and the second mounting pad 430 are affixed to a surface, the level 480 may be used to level-out the main body 410. When the main body 410 is level, the user can lock the main body 410 in a level position using the first locking knob 440 and the second locking knob 460. Thus, a user of the apparatus 400 can attach the mounting pads 420, 430 and main body 410 to surface in a near level position and then fine tune the level of the apparatus 400 by loosing the locking knob 440 on the first end and pivoting the apparatus 400 until level is achieved. Once level is achieved, the first locking knob 440 is tightened.

A reference strip 470 is also associated with the main body 410. The reference strip 470 is made of metal or any other X-ray absorbing or X-ray reflecting material. The material need only be differentiable from the surrounding environment. Similarly, the main body 410, the first mounting pad 420, the second mounting pad 430, the first locking knob 440, and the second locking knob 460 can be made plastic or any other material that permits X-rays to substantially pass unattenuated. The reference strip 470 can be formed into various shapes; for example, the reference strip 470 can be a simple line, a cross-hairs, or include reference marks/ticks. The reference strip 470 is either attached to or embedded in the main body 410 so that when the level 480 reads "level" (i.e. 90 degrees off of plumb) the reference strip 470 is also level.

When the X-ray reference apparatus 400 is affixed to a cassette holder and the film is exposed, an image of the reference strip 470 will appear in the exposure, thus giving a radiologist, or other medical professional, a reference to perfectly level with regard to the X-ray image of the patient. Alternatively, the X-ray reference apparatus 400 can be affixed to a person. Hence, an image of the reference strip 470 can be used as a reference relative to the physical circumstances of the exposure. For example, X-ray film is not always loaded level to the floor upon which a patient is standing during an exposure. When the X-ray reference apparatus 400 is used during an exposure, a reference mark which is certain to be level now appears in the image. Advantageously, the radiologist or other medical professional can use the reference mark to analyze the image.

The reference strip 470 may also be used to assist in leveling the cassette holder on an X-ray machine, or after installation of the X-ray machine. This is done by taking an X-ray of the level reference strip 470 and comparing this to an edge of the X-ray film. The reference strip 470 should be perfectly parallel to the bottom edge of the exposed film if the cassette holder is installed level. If however, the reference strip is not parallel with the bottom of the exposed film, adjustments are made to the cassette holder to correct it. A follow-up X-ray with the level reference strip is then taken to confirm that the cassette holder is level, or if further correction is needed. Thus, redundancies can be built into the system to ensure a level reference is made. For example, the reference strip 470 will be level, as will the cassette holder holding the X-ray film. All of these increase the precision and accuracy of X-rays taken over a period of time.

Figure 5:
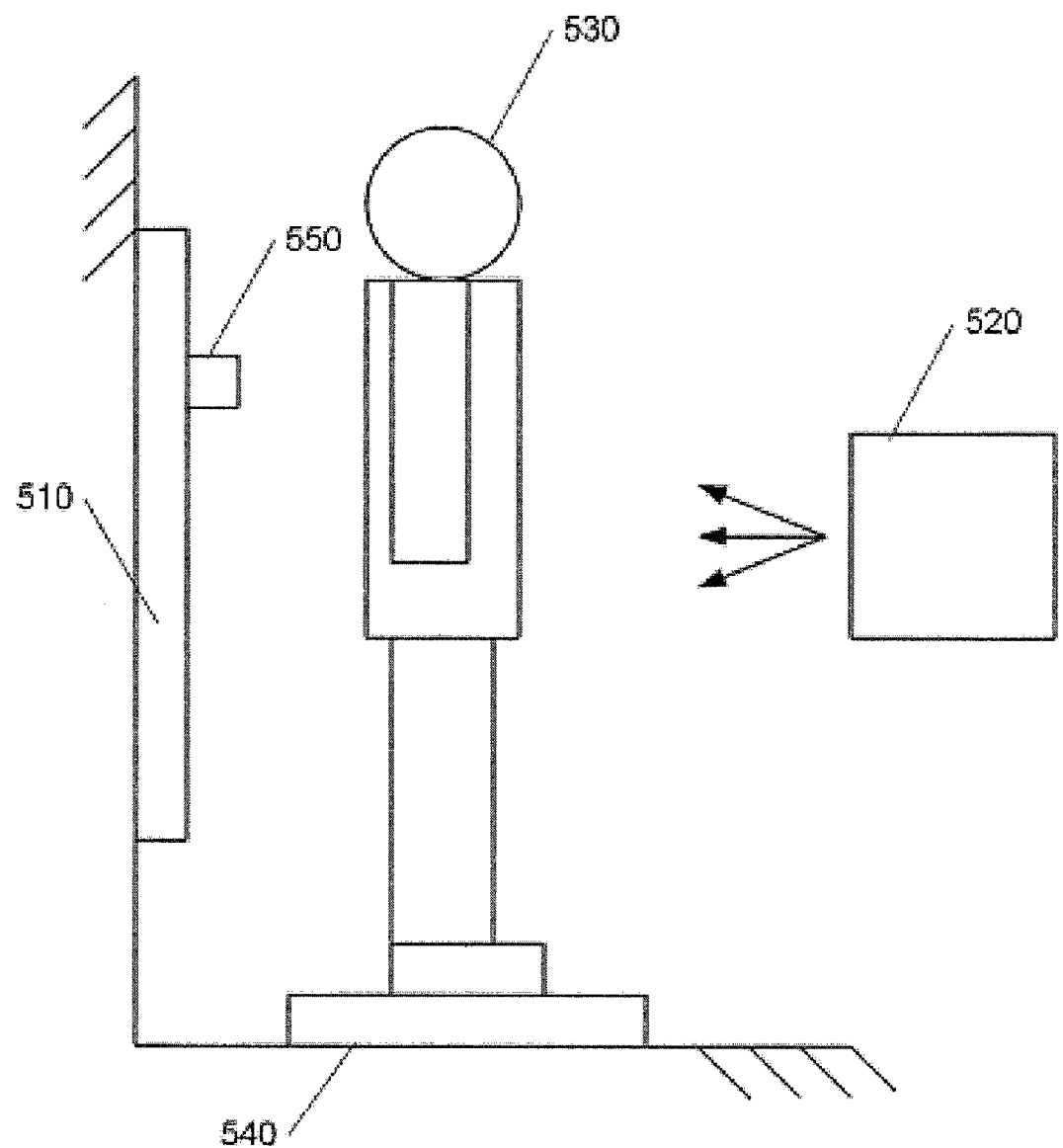
FIG. 5 is a depiction of a patient positioning apparatus in use with a X-ray reference apparatus.

Referring now to FIG. 5, a depiction of a patient positioning apparatus in use with an X-ray reference apparatus in an X-ray room is shown. The X-ray room includes a cassette holder 510 and an X-ray source 520. During an X-ray exposure, a patient 530 stands between the cassette holder 510 and the X-ray source 520.

The cassette holder 510 holds a film cassette or cartridge, which in turn holds the X-ray film. The cassette holder 510 is usually mounted on the wall or to a post or tube that allows for vertical positioning. The X-ray source 520, which can also be moved, is usually positioned some distance away from the cassette holder 510. The cassette holder 510 and X-ray source 520 are adjusted so that the exposure will image the correct body part of the patient 530. In some embodiments, the distance of the X-ray source 520 to the cassette holder 510 from about 40 to about 72 inches.

A patient positioning apparatus 540 is positioned on the floor in front of the cassette holder 510. The position of the patient positioning apparatus 540 is either secured or marked and recorded on the floor so that the patient positioning apparatus 540 can always be returned to the same place. The user then adjusts the feet 120 of the patient positioning apparatus 540 so that the dome level reads level. The user can also place an X-ray reference apparatus 550 on the cassette holder 510. The X-ray reference apparatus 550 is leveled-out as described above. The angle of the turntable of the patient positioning apparatus 540 is adjusted according to the X-ray orders of the radiologist or other medical professional. The patient 530 stands on the patient positioning apparatus 540 and the X-ray images are taken.

Figure 6:
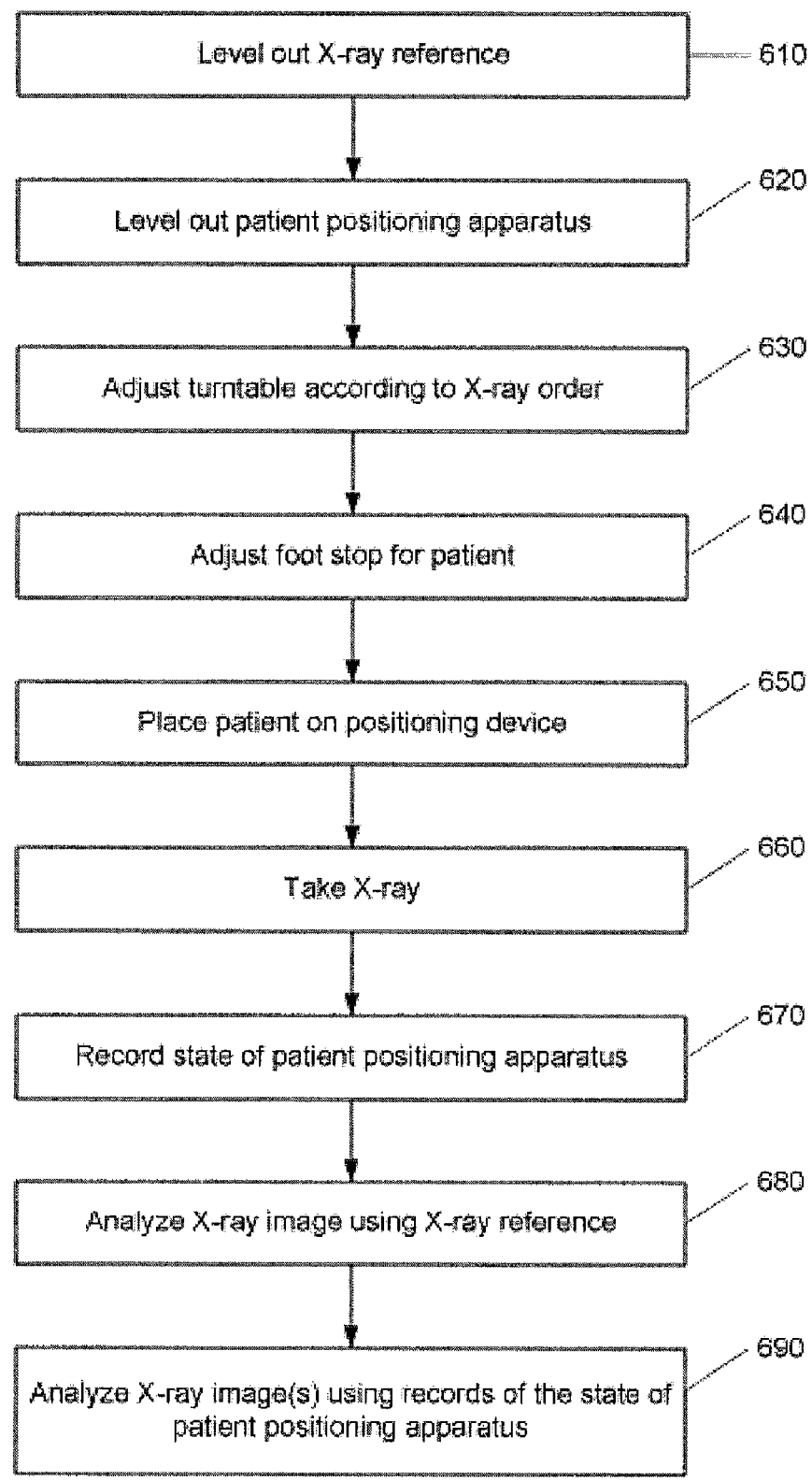
FIG. 6 is a flowchart of a method of using a patient positioning apparatus and a X-ray reference apparatus.

Referring now to FIG. 6, a flowchart of a method of using a patient positioning apparatus 100 and an X-ray reference apparatus 400 is shown. Though all of these steps may not be completed every time a patient is X-rayed, for example the leveling may already have been done and simple check of the bubble level is all that is needed, the flow chart is provided merely as a sample of the overall process. In an X-ray reference setup operation 610, the user levels out the main body of an X-ray reference apparatus as described above. In a patient position apparatus setup operation 620, the user places a patient positioning apparatus in front of a cassette holder in a known position. The user levels out the patient positioning apparatus as described above.

In a patient position apparatus adjustment operation 630, the user adjusts the angle of the turntable of the patient position apparatus according to the medical professional's X-ray orders. In a heel stop operation 640, the user adjusts the position of the heel stop according to the size of the patient's feet, and or body size. In a patient positioning operation 650, the user places the patient on the patient position apparatus. The professional instructs the patient to keep his feet tight up against the foot guides of the patient position apparatus. The patient is now restricted in his or her movement, and accurate, repeatable X-rays can be taken in a precise and efficient manner.

In an X-ray operation 660, the user takes an X-ray by exposing a sheet of film with X-rays from an X-ray source. In a referencing operation 670, the user records the position of the turntable of the patient position apparatus and associates this record with the exposed X-ray film.

After the X-ray film is developed, in an X-ray reference mark analysis operation 670, the radiologist, or other medical professional, uses the image of the reference strip from the exposure of the X-ray reference in making a diagnosis. The reference strip also aids the radiologist or medical professional in performing precise radiological measurements or mensuration. In an X-ray position analysis operation 680, the recorded position of the patient position apparatus is used to aid in making a diagnosis. In some cases the recorded position for a single X-ray assists in a diagnosis. For instance, when a precise angle of the spine is used to take oblique x-rays of the spine, the bone and/or joints should present in a specific manner in an X-ray image, and variances from that specific manner can form the basis for a diagnosis. Also, the recorded position of the patient positioning apparatus over multiple X-rays eliminates common positioning errors, and assists in making a diagnosis. For instance, the change in spinal, or other bone and/or joint positioning over time can be recorded to determine the efficacy of treatment or progression of disease states. Accurate leg length studies can also be done knowing the patient positioning apparatus and the X-ray reference apparatus are both level. Such analyses are possible as the patient position has been imaged consistently and repeatably, using the patient position apparatus.

Advantageously, the patient positioning apparatus and method allow a medical professional to easily determine the angle of the patient's feet relative to the base. Additionally, the patient positioning apparatus can be easily adjusted to compensate for different foot sizes and body sizes. This improves efficiency by eliminating the need to reposition the patient multiple times prior to taking the X-ray. Unlike most restraining devices, the patient positioning apparatus can be used with any body type. Moreover, the patient positioning apparatus encourages the patient to stand at a specific angle relative to the base and in a specific manner which promotes consistency amongst X-rays taken over time. Further, the medical professional can use the X-ray reference and its associated reference marks to easily and effectively analyze images. Compared to existing restraints, the patient positioning apparatus and method are inexpensive, quick to setup, and easy to use. The patient positioning apparatus saves the user time, provides the doctor with precision positioning and analysis, and helps prevent unnecessary retakes due to positioning errors which translates into less X-ray exposure for the patient.

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. For example, the described exemplary embodiments focused on an implementation using film-based radiology; however, those skilled in the art will also recognize that the invention can be used with digital X-ray systems. Additionally, the shape of the apparatuses can be altered significantly without deviating from the spirit of the invention. For example, the foot guides, turntable, and stop can be made ergonomic. Those skilled in the art will also recognize that this invention is not restricted to the field of chiropractics or to only human use. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An apparatus comprising:
a base;
a turntable, wherein the turntable is rotatably attached to the base;
a foot guide; and
a level;
wherein,
the apparatus is capable of positioning a patient for X-ray exposure.

2. The apparatus of claim 1, wherein the foot guide comprises two side plates and a heel stop.

3. The apparatus of claim 1, further comprising a locking knob; wherein the locking knob is capable of preventing the turntable from rotating.

4. The apparatus of claim 1, further comprising adjustable feet.

5. The apparatus of claim 1, wherein the base has graduation marks and the turntable has a reference mark; such that the graduation marks and the reference mark indicate the angle of the turntable relative to the base.

6. An apparatus comprising:
a main body;
a first mounting pad;
a second mounting pad; and
a reference strip;
wherein;
the apparatus is an X-ray image leveling apparatus;
an image of the reference strip appears on the X-ray image; and
the first and second mounting pads affix the main body to a surface.

7. The apparatus of claim 6, further comprising a level.

8. The apparatus of claim 6, wherein the main body, the first mounting pad, and the second mounting pad are made of X-ray transparent materials.

9. The apparatus of claim 6, wherein the body is attached to the first mounting pad via a first locking knob.

10. The apparatus of claim 6, wherein the body is attached to the second mounting pad via a second locking knob.

11. The apparatus of claim 6, wherein the body is attached to the first mounting pad via a first locking knob, and the body is rotatably connected to the second mounting pad.

12. A method for taking X-rays, comprising:
positioning a patient using a patient positioning apparatus at a specific angle to an X-ray machine;
exposing the patient to an X-ray source; and
acquiring an X-ray image;
wherein,
the patient positioning apparatus comprises a base; a turntable, a level, and a foot guide;
the turntable is rotatably attached to the base; and
the patient's feet are in contact with the foot guide during the exposure of the X-ray source.

13. The method of claim 12, further comprising:
analyzing the X-ray using knowledge of the specific angle.

14. The method of claim 12, further comprising:
analyzing a series of X-rays using knowledge of the specific angle of each X-ray of the series.

15. A method for referencing a level in an X-rays image, comprising:
leveling an X-ray reference; and
acquiring an X-ray image;
wherein,
the X-ray reference comprises a main body; a first mounting pad; a second mounting pad; and, a reference strip, wherein an image of the reference strip appears on the X-ray image.

16. The method of claim 15, further comprising:
analyzing the X-ray using the image of the reference strip.

17. The method of claim 15, wherein the X-ray image is of a patient.

18. A method comprising:
using an X-ray reference to aid in leveling a cassette holder associated with an X-ray machine after installation of the X-ray machine,
wherein, the X-ray reference comprises:
a main body;
a first mounting pad;
a second mounting pad;
a level and,
a reference strip, and
an image of the reference strip appears on an X-ray images.

19. The method of claim 18, wherein the method further comprises:
comparing the image of the reference strip on an X-ray film with an edge of the X-ray film;
determining if the cassette holder is level; and
making any needed leveling adjustments to the cassette holder.

* * * * *